(12) United States Patent
Sung et al.

(10) Patent No.: US 10,939,874 B2
(45) Date of Patent: Mar. 9, 2021

(54) DEEP-LEARNING-BASED CANCER CLASSIFICATION USING A HIERARCHICAL CLASSIFICATION FRAMEWORK

(71) Applicant: THE REGENTS OF THE UNIVERSITY OF CALIFORNIA, Oakland, CA (US)

(72) Inventors: Kyung Hyun Sung, Los Angeles, CA (US); William Hsu, Westlake Village, CA (US); Shiwen Shen, Los Angeles, CA (US); Xinran Zhong, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 272 days.

(21) Appl. No.: 16/104,131

(22) Filed: Aug. 16, 2018

(65) Prior Publication Data
US 2019/0183429 A1    Jun. 20, 2019

Related U.S. Application Data

(63) Continuation of application No. PCT/US2017/024071, filed on Mar. 24, 2017.
(Continued)

(51) Int. Cl.
*A61B 5/00* (2006.01)
*A61B 5/055* (2006.01)
(Continued)

(52) U.S. Cl.
CPC ............ *A61B 5/7267* (2013.01); *A61B 5/055* (2013.01); *A61B 5/4381* (2013.01); *G06K 9/42* (2013.01);
(Continued)

(58) Field of Classification Search
CPC ..... A61B 5/7267; A61B 5/4381; A61B 5/055; A61B 5/4244; A61B 5/201; A61B 5/08;
(Continued)

(56) References Cited

U.S. PATENT DOCUMENTS 8,139,831 B2    3/2012    Khamene
8,185,485 B2    5/2012    Keith
(Continued)

FOREIGN PATENT DOCUMENTS

| CN | 104834943 A | 8/2015 |
|---|---|---|
| WO | 2014207627 A1 | 12/2014 |
| WO | 2015042421 A1 | 3/2015 |

OTHER PUBLICATIONS

ISA/US, United States Patent and Trademark Office (USPTO), International Search Report and Written Opinion dated Jun. 15, 2017, related PCT international application No. PCT/US2017/024071 pp. 1-8, claims searched pp. 9-13.
(Continued)

*Primary Examiner* — Amandeep Saini
(74) *Attorney, Agent, or Firm* — O'Banion & Ritchey LLP; John P. O'Banion

(57) ABSTRACT

An automatic classification method for distinguishing between indolent and clinically significant carcinoma using multiparametric MRI (mp-MRI) imaging is provided. By utilizing a convolutional neural network (CNN), which automatically extracts deep features, the hierarchical classification framework avoids deficiencies in current schemes in the art such as the need to provide handcrafted features predefined by a domain expert and the precise delineation of lesion boundaries by a human or computerized algorithm. This hierarchical classification framework is trained using previously acquired mp-MRI data with known cancer classification characteristics and the framework is applied to
(Continued)

mp-MRI images of new patients to provide identification and computerized cancer classification results of a suspicious lesion.

21 Claims, 3 Drawing Sheets

Related U.S. Application Data

(60) Provisional application No. 62/312,946, filed on Mar. 24, 2016.

(51) Int. Cl.

| | | |
|---|---|---|
| *G06T 7/00* | (2017.01) | |
| *G06K 9/42* | (2006.01) | |
| *G06K 9/52* | (2006.01) | |
| *G06K 9/62* | (2006.01) | |
| *G06K 9/66* | (2006.01) | |
| *A61B 5/20* | (2006.01) | |
| *A61B 5/08* | (2006.01) | |

(52) U.S. Cl.
CPC ............ *G06K 9/527* (2013.01); *G06K 9/6269* (2013.01); *G06K 9/66* (2013.01); *G06T 7/0012* (2013.01); *A61B 5/08* (2013.01); *A61B 5/201* (2013.01); *A61B 5/4244* (2013.01); *G06T 2207/10088* (2013.01); *G06T 2207/20081* (2013.01); *G06T 2207/20084* (2013.01); *G06T 2207/30096* (2013.01)

(58) Field of Classification Search
CPC ......... G06T 7/0012; G06T 2207/30096; G06T 2207/10088; G06T 2207/20084; G06T 2207/20081; G06K 9/42; G06K 9/527; G06K 9/6269; G06K 9/66; G16H 50/70
USPC .......................................................... 382/131
See application file for complete search history.

(56) References Cited

U.S. PATENT DOCUMENTS

| | | | |
|---|---|---|---|
| 2013/0322728 A1* | 12/2013 | Jacobs | ................... A61B 5/055 382/132 |
| 2014/0073907 A1 | 3/2014 | Kumar | |
| 2014/0153807 A1 | 6/2014 | Seong | |
| 2015/0254555 A1 | 9/2015 | Williams, Jr. | |
| 2016/0048972 A1 | 2/2016 | Kam | |
| 2017/0116387 A1 | 4/2017 | El-Zehiry | |

OTHER PUBLICATIONS

Liao, Shu et al., "Representation Learning: A Unified Deep Learning Framework for Automatic Prostate MR Segmentation", Med. Image Comput Comput Assist Interv. 2013; 16 (0 2): 254-261.

Ovalle, John Edilson Arevalo, "Representation learning for histopathology image analysis", Universidad Nacional de Colombia, Thesis, 2013, 81 pages.

Litjens, Geert et al., "Deep learning as a tool for increased accuracy and efficiency of histopathological diagnosis", Scientific Reports (2016), 23 pages, published online May 23, 2016.

Fehr, Duc et al., "Automatic classification of prostate cancer Gleason scores from multiparametric magnetic resonance images", Proceedings of the National Academy of Sciences, 2015, 112(46): E6265-E6273, published online Nov. 2, 2015.

Wibmer, Andreas et al., "Haralick texture analysis of prostate MRI: utility for differentiating non-cancerous prostate from prostate cancer and differentiating prostate cancers with different Gleason scores", Eur. Radiol., vol. 25, No. 10, pp. 2840-2850, Oct. 2015.

Tiwari, Pallav et al., "Multi-kernel graph embedding for detection, Gleason grading of prostate cancer via MRI/MRS", Medical image analysis 17(2): 219-235, Feb. 2013.

Ciompi, Francesco, et al., "Automatic classification of pulmonary peri-fissural nodules in computed tomography using an ensemble of 2D views and a convolutional neural network out-of-the-box", Medical image analysis 26.1 (2015): 195-202, published online Sep. 8, 2015.

Razavian, Ali et al, "CNN features off-the-shelf: an astounding baseline for recognition", Proceedings of the IEEE Conference on Computer Vision and Pattern Recognition Workshops, pp. 1-8, May 12, 2014.

Carneiro, Gustavo et al., "Unregistered Multiview Mammogram Analysis with Pre-trained Deep Learning Models", Medical Image Computing and Computer-Assisted Intervention—MICCAI 2015, Springer International Publishing, 2015, pp. 652-660.

European Patent Office (EPO), Extended European Search Report dated Aug. 9, 2019, related European patent application No. 17771257.7, pp. 1-6, claims searched, pp. 7-11.

Khalvati, Farzad et al., "Automated prostate cancer detection via comprehensive multi-parametric magnetic resonance imaging texture feature models", BMC Medical Imaging (2015) 15:27, Aug. 5, 2015, pp. 1-14.

Chung, Audrey G. et al., "Discovery Radiomics for Multi-Parametric MRI Prostate Cancer Detection", Aug. 31, 2015, XP055480699, retrieved from the Internet: URL: https://arxiv.org/pdf/1509.00111.pdf, pp. 1-8.

\* cited by examiner

DEEP-LEARNING-BASED CANCER CLASSIFICATION USING A HIERARCHICAL CLASSIFICATION FRAMEWORK

CROSS-REFERENCE TO RELATED APPLICATIONS

This application is a 35 U.S.C. § 111(a) continuation of PCT international application number PCT/US2017/024071 filed on Mar. 24, 2017, incorporated herein by reference in its entirety, which claims priority to, and the benefit of, U.S. provisional patent application Ser. No. 62/312,946 filed on Mar. 24, 2016, incorporated herein by reference in its entirety. Priority is claimed to each of the foregoing applications.

The above-referenced PCT international application was published as PCT International Publication No. WO 2017/165801 on Sep. 28, 2017, which publication is incorporated herein by reference in its entirety.

STATEMENT REGARDING FEDERALLY SPONSORED RESEARCH OR DEVELOPMENT

This invention was made with Government support under 1436827, awarded by the National Science Foundation. The Government has certain rights in the invention.

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to medical diagnostic imaging methods, and more particularly to deep-learning based magnetic resonance imaging methods that can accurately identify, localize, assess risk and stage cancers, such as prostate cancer. While the technology is discussed in the context of prostate cancer, the methods using the pre-trained deep network can be used in a variety of clinical domains such as breast, lung, kidney and liver cancer.

2. Background Discussion

The identification of abnormal anatomical structures and cancerous lesions in the body of a patient depends heavily on the imaging system capabilities and the experience and skill of the analyst. Early identification of cancers can allow early diagnosis and intervention resulting in lower cancer specific mortality.

Accurate cancer classification is often a difficult task because of the ambiguous appearance of lesions that are regularly observed on diagnostic imaging studies. Clear imaging is also necessary for accurate tumor localization during targeted biopsies. In some cases, sufficient diagnostic imaging can result in the deferral of a biopsy or may even avoid the biopsy altogether in selected patients. For example, prostate cancer is a leading cause of cancer-related death in men in the United States and a biopsy is the current standard diagnostic tool for tumor classification.

In prostate cancer, the Gleason Score classification is a measure of aggressiveness: a higher Gleason Score indicates a worse prognosis. The Gleason Score is a system of classifying prostate cancer cells based on how abnormal they look under a microscope compared to normal cells. The Gleason classification ranges from 2 to 10 and each grade level is also an objective indication of how likely the tumor will spread. The Gleason score is based on the appearance of the two most common cell morphologies. The scores of the two most common morphologies are combined to produce the total Gleason grade. Unfortunately, the Gleason grading system can assign the same score to significantly different risk groups and therefore other grading systems have been proposed.

Although the Gleason system has a scale of 2-10, scores 2-5 are no longer assigned in practice and the lowest score that is now assigned is a 6. This scoring can cause confusion in patients who assume that their cancer is serious because their cancer is in the middle of the scale and that aggressive treatment may be needed. Nevertheless, this grading plays an important role in the treatment decisions of the treating physicians. Grading systems may also differ for each type of cancer.

However, prostate cancer is challenging to diagnose because biopsies do not provide a uniform and accurate sampling of the prostate tissue, leading to high false positive rates and potential overtreatment. Differentiating a clinically significant lesion from an indolent lesion is an important task for accurate prostate cancer classification and appropriate treatment determinations.

Magnetic resonance imaging (MRI) is a noninvasive diagnostic imaging system that that physicians can use to diagnose and treat medical conditions. However, the MRI cannot detect all prostate tumors and has shown poor sensitivity for imaging low volume Gleason (3+3) tumors. Multiparametric magnetic resonance imaging (mp-MRI) is an imaging scheme with functionality that supplements standard anatomical T1 and T2 weighted imaging. MRI imaging can also be very challenging and often requires a significant amount of post processing and analysis by very experienced radiologists because of low imaging sensitivity.

One well identified limitation of mp-MRI is that the tumors or nodules may not be clearly demarcated or encapsulated because the margins of the nodules are indistinct in the image. Accurate identification of lesions permit targeted biopsies that can improve the assignment of appropriate treatment options. Accurate imaging can also reduce unnecessary biopsies and prevent overdiagnosis and overtreatment.

Although multi-parametric MRI is a promising imaging modality for the detection and grading of prostatic carcinoma, current mp-MRI scoring systems, such as PI-RADS, are generally subjective and have a limited ability to distinguish between indolent and clinically significant cancers. Automatic classification algorithms to improve the current scoring systems are an active research area but typically require precise delineation of suspicious lesion boundaries, anatomical information, and carefully designed handcrafted features (e.g., features predefined by a domain expert).

Accordingly, there is a need for precise imaging systems that are capable of accurately classifying the tumor Gleason Score or other scale to assist radiologists with staging lesions and have an impact on treatment selection and outcomes as well as avoiding unnecessary biopsies and their risks of complications.

BRIEF SUMMARY

The present technology provides a deep-learning-based computerized cancer classification system and method using magnetic resonance imaging and preferably using multi-parametric magnetic resonance imaging (mp-MRI). The hierarchical classification framework avoids (1) the need to provide handcrafted features (e.g., features predefined by a domain expert) as well as (2) the need for precise segmentation of cancerous lesions (e.g., exact delineation of lesion boundaries by a human or computerized algorithm).

These deficiencies are avoided by utilizing a convolutional neural network (CNN), which automatically extracts deep features. This hierarchical classification framework is trained using previously acquired mp-MRI data with known cancer classification results (e.g., indolent vs. clinically significant cancer) and is applied to new patients with mp-MRI to provide computerized cancer classification results of a suspicious lesion.

One preferred embodiment uses a pre-trained convolution neural network (CNN) as a feature extractor to overcome the issue of having limited training samples (e.g., datasets that have been labeled with outcome information), which is often the case in the medical domain. Furthermore, instead of a precise contour of the lesion, the method only requires approximate image patches containing the lesion as input (e.g., versus precise lesion boundaries), which is much more convenient and robust. Finally, the method combines the outputs of classifiers in a layered manner, providing a more efficient way to combine features from deep learning and conventional clinical features. This hybrid approach allows the incorporation of additional features beyond imaging and results from multiple modalities as inputs to generate a final classification: this two-step classification approach yields higher accuracy compared to using a single classification step.

A specific example of this concept is to provide improved classification between indolent and clinically significant prostate cancer based on Gleason Score (GS), where the indolent prostate cancer cases were defined as GS smaller or equal to six (GS≤6) while the clinically significant prostate cancer cases were defined as GS larger or equal to seven (GS≥7). In this implementation, standard prostate mp-MRI data acquired at 3.0 T systems are used; including T2-weighted (T2w) imaging, diffusion-weighted imaging (DWI), and dynamic contrast-enhanced MRI (DCE-MRI). In particular, T2w, apparent diffusion coefficient (ADC) and $K^{trans}$ were used as input data to provide unique anatomical and functional information of the prostate. All the mp-MRI data are correlated with the whole mount histopathology, and all the lesions are matched with respect to location, size and GS as a ground truth.

In one embodiment described herein, a pre-trained CNN method may be used to alleviate the learning requirement. However, the method can incorporate both pre-trained and non-pre-trained CNN methods, depending on the availability of labeled training data that can attain sufficient feature learning. One CNN method known as OverFeat, for example, allows the use of deep learning out-of-the-box when limited training data sets are available as the deep features are pre-trained using a dataset of natural images (a set of 1.2 million natural images).

The preferred system and method for detecting and grading a carcinoma includes the steps of (i) acquiring a plurality of multi-parametric MRI (mp-MRI) images of a subject; (ii) preprocessing the images with pixel intensity normalization, pixel spacing normalization and rescaling to produce standardized small image patches; (iii) extracting deep learning features from T2-weighted (T2w), apparent diffusion coefficient (ADC) and $K^{trans}$ data of the standardized small image patches with convolution neural network (CNN); (iv) obtaining a prediction score for each set of deep learning features applying a first order classification of support vector machine (SVM) classifiers; and (v) applying a second order classification of a Gaussian radial basis function kernel SVM classification of combined first order classification data and skewness of intensity histogram, average and highest $10^{th}$ percentile standard imaging features to produce a final classification of an indolent or cancerous lesion.

It will be appreciated that the model-based approach is capable of accurately classifying the tumor Gleason Score to assist radiologists with staging lesions. The classification framework is capable of improving diagnostic accuracy by learning from the growing amounts of clinical and imaging data that are being collected as part of routine care.

According to one aspect of the technology, a method for classifying lesions is provided that utilizes deep learning methods to characterize the lesion in mp-MRI through a pre-trained convolutional neural network model.

Another aspect of the technology is to provide a method for classifying lesions that builds a hybrid two-order classification model that combines deep learning and conventional statistical features. Another aspect of the technology is to provide a method for classifying lesions that does not require precise lesion boundaries and anatomical-location-specific training.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWINGS

The technology described herein will be more fully understood by reference to the following drawings which are for illustrative purposes only.

DETAILED DESCRIPTION

Referring more specifically to the drawings, for illustrative purposes, embodiments of methods for cancer classification from diagnostic imaging are generally shown. Several embodiments of the technology are described generally in FIG. 1 and FIG. 2 to illustrate the system characteristics and functionality. It will be appreciated that the methods may vary as to the specific steps and sequence and the systems and apparatus may vary as to structural details without departing from the basic concepts as disclosed herein. The method steps are merely exemplary of the order that these steps may occur. The steps may occur in any order that is desired, such that it still performs the goals of the claimed technology.

Generally, an automatic classification method to distinguish between indolent and clinically significant prostatic carcinoma using multi-parametric MRI (mp-MRI) is used to illustrate the technology. Although the methods are demonstrated in the domain of prostate cancer, they can be adapted and applied to other types of cancer classification tasks, including breast, lung, kidney, and liver cancers.

The main contributions of the methods include: 1) utilizing a state-of-art deep learning methods to characterize a lesion in mp-MRI through a pre-trained convolutional neural network model; 2) building a hybrid two-order classification model that combines deep learning and conventional statistical features, and thereby 3) avoiding the need for precise lesion boundaries and anatomical-location-specific training.

Figure 1:
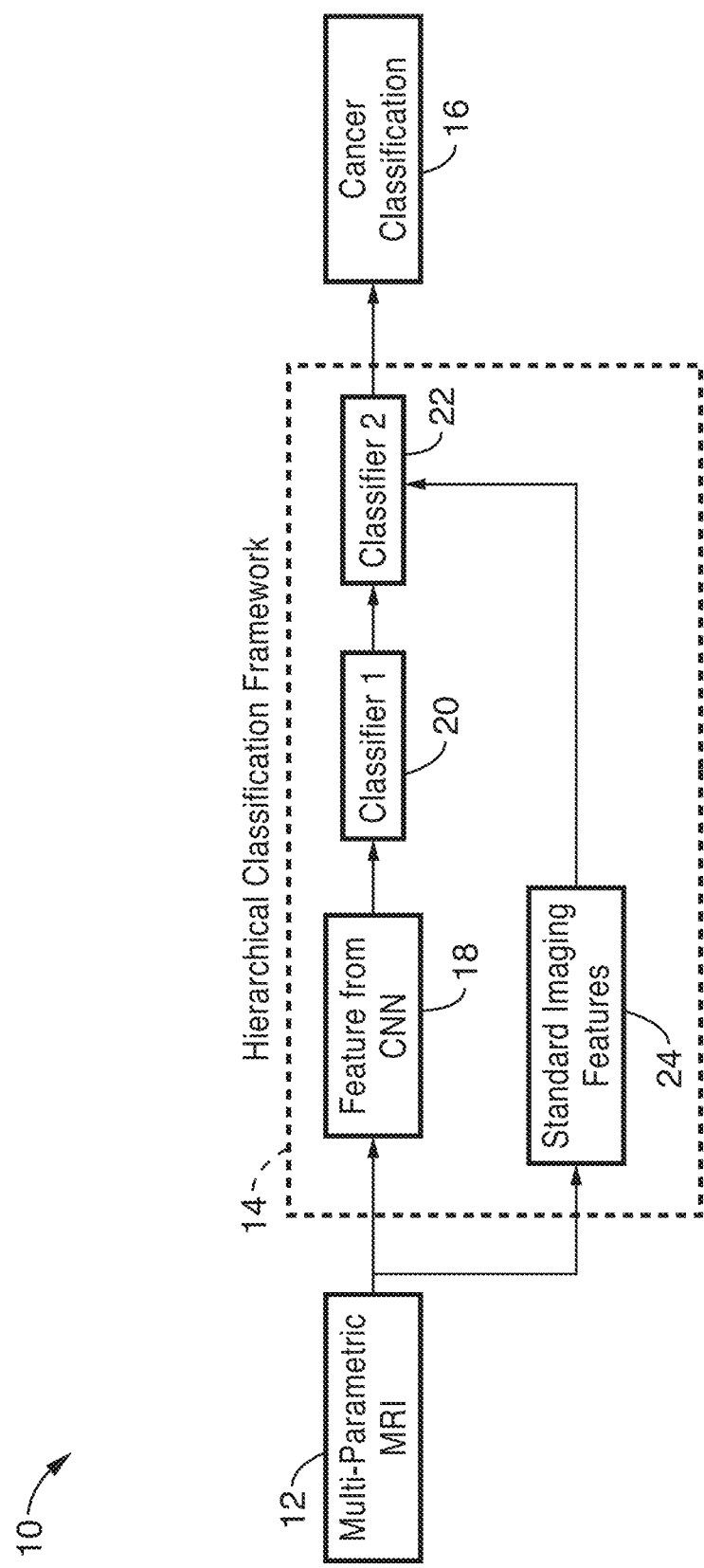
FIG. 1 is a functional block diagram of a classification method using mp-MRI and a hierarchical classification framework according to one embodiment of the technology.

Turning now to FIG. 1, a flow diagram of one embodiment of a method 10 for deep-learning-based hierarchical classification of cancers is shown schematically. Initially, multi-parametric MRI imaging is preferably used to acquire mp-MRI images of a target location of a subject such as the prostate at block 12. Multi-parametric MRI imaging of a subject includes supplemental forms of imaging to the standard anatomical T1 and T2 weighted imaging. These forms include T2-weighted (T2w) imaging, dynamic contrast-enhanced MRI (DCE-MRI) and diffusion-weighted imaging (DWI), along with the calculation of apparent diffusion coefficient (ADC) maps. Although multi-parametric MRI imaging at block 12 is preferred, imaging of some cancers such as breast cancer will not have this kind of magnetic resonance imaging input.

The preferred mp-MRI data that is obtained at block 12 of FIG. 1, preferably begins with T2-Weighted (T2w) sequences to delineate outlines and the presence of bleeding. T2w images (axial, coronal, and sagittal) are usually obtained with fast spin echo sequences such as 2D RARE (rapid acquisition with relaxation enhancement) pulse sequences.

Dynamic contrast-enhanced MRI (DCE-MRI) images are obtained from rapid T1w gradient echo scans taken before, during and following intravenous administration of a gadolinium-based contrast agent (GBCA). Diffusion-weighted imaging (DWI) normally includes an ADC map and high b-value images. An ADC map is a map of the calculated ADC values for each voxel in an image. ADC mean and DWI signal intensities may also be obtained.

The mp-MRI data that are acquired at block 12 are transformed with a hierarchical classification framework 14 to produce a classification value at block 16 of FIG. 1. This hierarchical classification framework 14 is trained using previously acquired mp-MRI data with known cancer classification results 16 (e.g., indolent vs. clinically significant cancer) and is applied to new patients with mp-MRI to provide computerized cancer classification results on a suspicious lesion.

Figure 2:
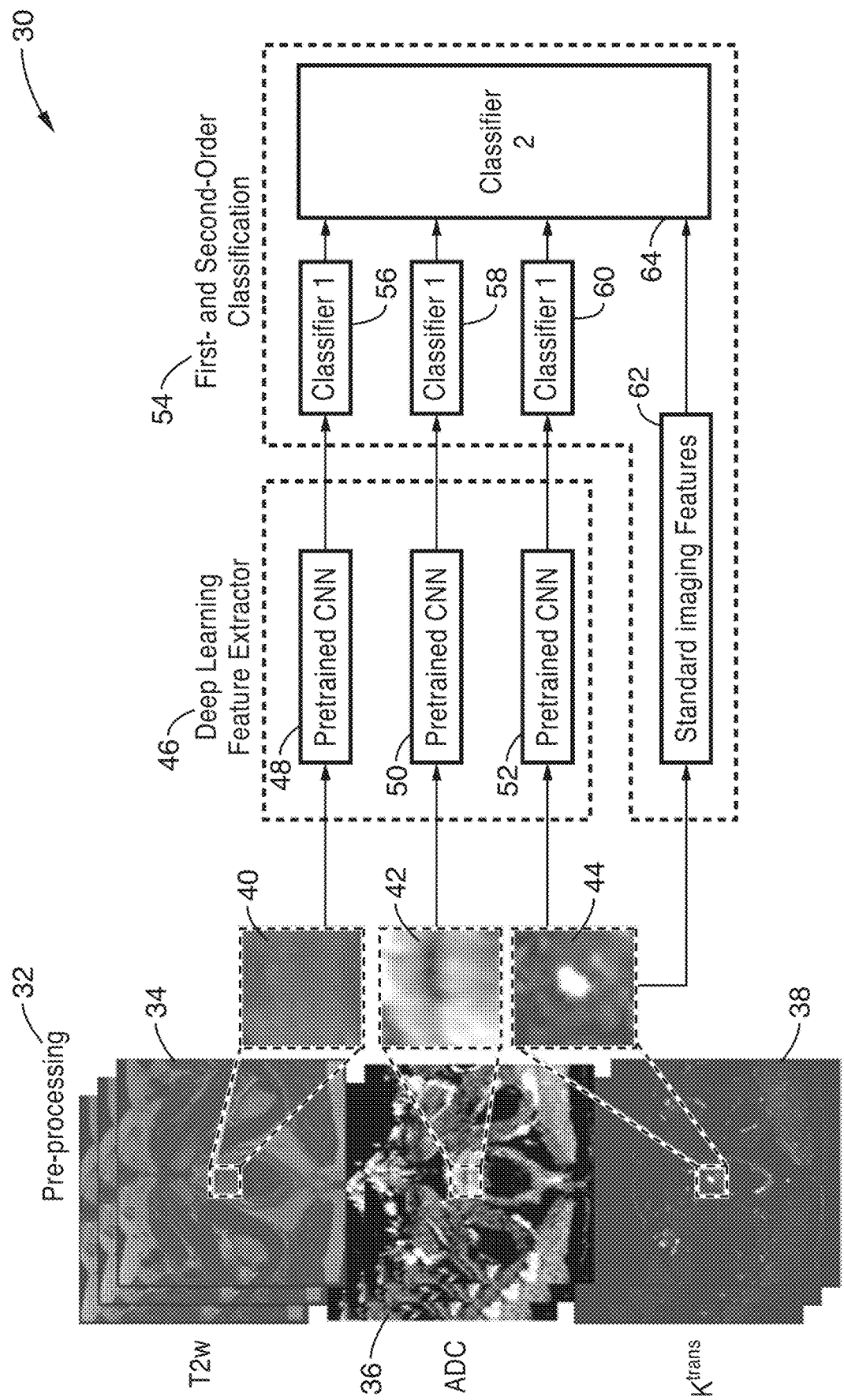
FIG. 2 is a functional block diagram of a deep-learning-based cancer classification method using mp-MRI and a hierarchical classification framework according to another embodiment of the technology.

As also shown in the illustration of FIG. 2, the small imaging patches for a suspicious lesion are defined as input data in T2w, ADC and $K^{trans}$ images. The output of the hierarchical classification framework 14 is the classification score 16 to be clinically significant prostate cancer for the suspicious lesion, for example.

The hierarchical classification framework 14 of FIG. 1 generally comprises three major components: (1) pre-processing, (2) a deep learning feature extraction 18, and (3) a first-order classification 20 and (4) a second-order classification 22. First, the pre-processing component preferably includes pixel intensity normalization, pixel spacing normalization and rescaling. The output of this step is the standardized small image patches, covering the entire suspicious lesion.

Second, the deep learning feature extractor 18 takes the standardized small image patches as input. A convolutional neural network is used to extract the deep features from T2w, ADC and $K^{trans}$ mp-MRI data. Here, the output of the 21 layer (the last convolutional layer) of the pre-trained CNN (e.g. OverFeat) can be used as the deep learning features.

Third, there are three linear support vector machine (SVM) classifiers (Classifier 1) 20 that are used in the first-order classification to obtain the prediction score for each set of deep features. The first-order classification is then combined with the other optional standard imaging features 24. Standard imaging features 24 may include: (a) skewness of intensity histograms in T2w images; (b) average ADC value; (c) lowest $10^{th}$ percentile; (d) ADC value; (e) average $K_{trans}$; (f) highest $10^{th}$ percentile $K_{trans}$ value; and (g) ROI size in T2w images.

The combined Classifier 1 and optional standard imaging features 24 are used as input for a Gaussian radial basis function kernel SVM classifier in the second-order classification (Classifier 2) 22, which outputs the final decision 16 (i.e. indolent vs. clinically significant prostate cancer).

Table 2 illustrates an example embodiment of Matlab computer program instructions that may be used for implementing the technology.

The technology described herein may be better understood with reference to the accompanying examples, which are intended for purposes of illustration only and should not be construed as in any sense limiting the scope of the technology described herein as defined in the claims appended hereto.

EXAMPLE 1

In order to demonstrate the operational principles of the apparatus and imaging and classification methods 30, a dataset of mp-MRI images were recorded for a total of 68 patients and processed using the processing steps shown generally in FIG. 1 and FIG. 2. A study cohort of 68 consecutive men who underwent 3.0T mp-MRI (Skyra and Trio, Siemens Healthcare) prostate imaging prior to radical prostatectomy was acquired. Each mp-MRI study, including T2-weighted (T2w), DWI and DCE images, was correlated with whole mount histopathology by experienced GU pathologists, and lesions were matched with respect to location, size and Gleason Score (GS). Indolent PCa cases were defined as having a GS smaller than seven (GS≤6) and cancerous (CS) PCa ones were defined has having a GS that was larger or equal to seven (GS≥7). A total of 102 lesions were identified, including 48 indolent and 54 CS sub-cohorts.

As shown schematically in FIG. 2, the acquired images were initially preprocessed 32 to produce base T2w images 34, ADC images 36 and $K^{trans}$ images 38. The middle slice of regions of interest (ROIs), suspicious for prostate cancer (PCa) in T2w, ADC and DCE ($K^{trans}$) images (annotated by patch squares 40, 42 and 44 respectively), were interpolated and rescaled to 512×512 pixels.

Two training stages (deep learning feature extraction 46 and first and second order classifications 54) were used to obtain the final decision in the embodiment 30 of FIG. 2. In the first stage 46, pre-trained CNN's (OverFeat) were used to overcome the small sample size. Deep features from the last convolutional layer (the 21 layer in OverFeat) were employed for each T2w ($f_{T2}$) extraction 48, ADC ($f_{ADC}$) extraction 50 and $K^{trans}$ ($f_K$) image extraction 52 separately. Three linear SVM classifiers 48, 50, 52 that were produced were then adopted to train $f_{T2}$, $f_{ADC}$ and $f_K$ respectively.

In the second stage 54, the decision values from the three classifiers 56, 58, 60 were combined with six statistical features 62 to train a Gaussian radial basis function (RBF) kernel SVM classifier 64, which produced an output of the final decision (indolent vs. CS). Statistical features ($f_s$) 62 included skewness-of-intensity histogram in T2w images, average ADC value, lowest $10^{th}$ percentile ADC value, average $K^{trans}$, highest $10^{th}$ percentile $K^{trans}$ value, and ROI size in T2w images.

The training process was generally designed as follows. First, the whole dataset was randomly divided into five folds of similar size. One fold was then selected as test set $IMAGE_{test}$ and the other four folds were training set $IMAGE_{train}$. After this, $IMAGE_{train}$ was equally and randomly divided into two phases, $IMAGE_{train1}$ and $IMAGE_{train}2$. $IMAGE_{train1}$) was employed to train the three linear SVMs in Stage 1 with leave-one-out cross-validation for selecting the optimal parameters. Once trained, the three trained classifiers were applied to $IMAGE_{train2}$, to generate prediction score vectors. With the prediction scores and $f_s$, $IMAGE_{train2}$ was used to train the RBF SVM in Stage 2 and the performance of the prediction was measured on $IMAGE_{test}$. The whole procedure was repeated five times (known as five-fold cross-validation), where each fold was used as a test set once. The final classification results are the average performance of the five-fold cross-validation of Example 2.

EXAMPLE 2

To demonstrate the effectiveness of the system, the four classification models were built and compared. Specifically, four different SVMs were built using only $f_s$, $f_{T2}$, $f_{ADC}$ or $f_K$, respectively. The performance of these models was also evaluated with a five-fold cross validation using the whole dataset. The results were measured using the mean areas under curve, mean accuracy, mean sensitivity and mean specificity as shown in Table 1.

Figure 3:
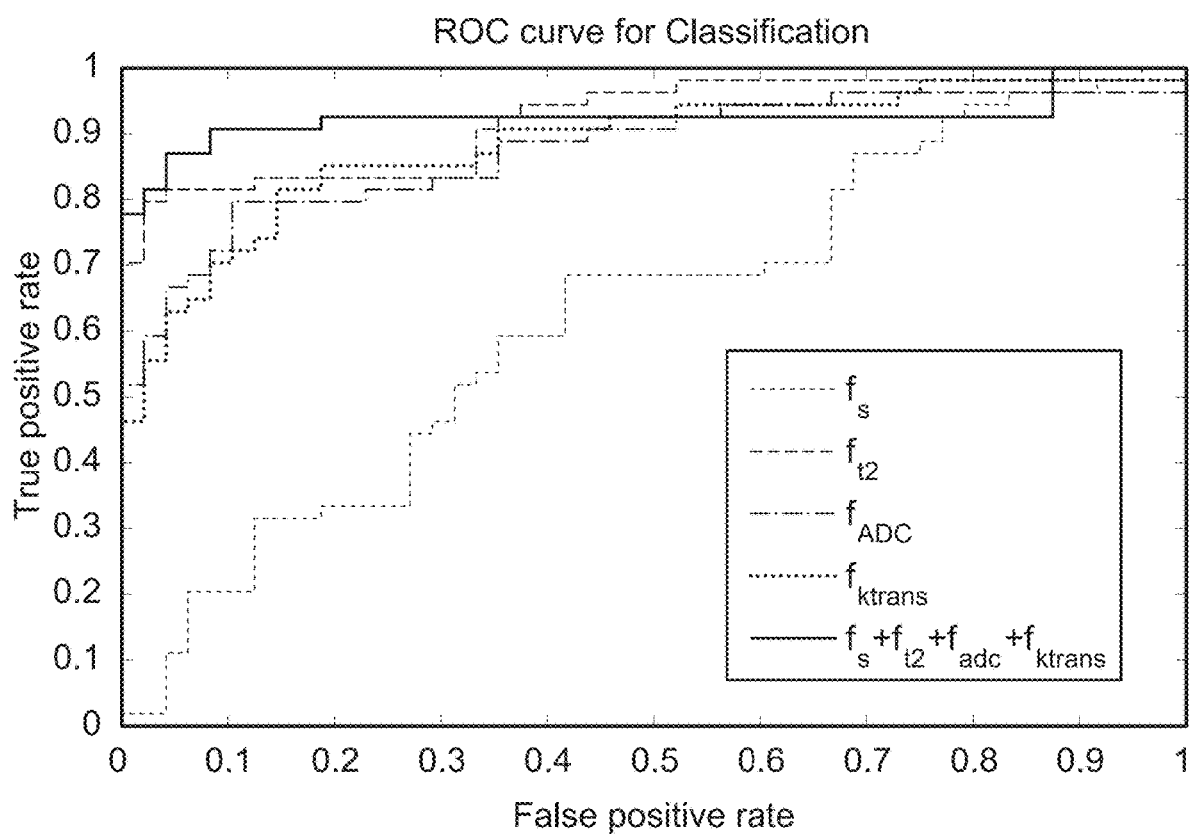
FIG. 3 is a graph of receiver operating characteristic (ROC) curve comparisons of four different SVMs. The described model achieved the highest performance compared to the other models built using only $f_s$, $f_{T2}$, $f_{ADC}$ or $f_K$, respectively.

FIG. 3 is a graph depicting the receiver operating characteristic (ROC) curves for the four models in this example. The model of the system ($f_s+f_{T2}+f_{ADC}+f_K$) shown in a solid line in FIG. 3 achieved the highest performance compared to the other models. It can be seen from FIG. 3 and Table 1 that the standard model using six statistical features ($f_s$) achieved the lowest performance mainly due to lack of accurate lesion contours and anatomical-location-specific training. The results also suggest that deep features significantly contribute to the improvement of the performance.

It can also be seen that the system achieves significantly higher accuracy over the others for distinguishing indolent vs. clinically significant PCa without requiring precise segmentation of lesion boundaries nor requiring location-specific training. The method has the potential to improve subjective radiologist based performance in the detection and grading of suspicious areas on mp-MRI.

From the description herein, it will be appreciated that the present disclosure encompasses multiple embodiments which include, but are not limited to, the following:

1. An apparatus for detecting and grading carcinoma, comprising: (a) a computer processor; and (b) a non-transitory computer-readable memory storing instructions executable by the computer processor; (c) wherein the instructions, when executed by the computer processor, perform steps comprising: (i) acquiring a plurality of multi-parametric MRI (mp-MRI) images of a subject; (ii) pre-processing the mp-MRI images to produce standardized small image patches; (iii) extracting deep learning features from T2-weighted (T2w), apparent diffusion coefficient (ADC) and $K^{trans}$ data of the standardized small image patches with a convolution neural network (CNN) method; (iv) obtaining a prediction score for each set of deep learning features by applying a first order classification of support vector machine (SVM) classifiers; and (v) applying as second order classification of a Gaussian radial basis function kernel SVM classification of combined first order classification data to produce a final classification.

2. The apparatus of any preceding embodiment, wherein the pre-processing of mp-MRI images instructions further comprise pre-processing the mp-MRI images with pixel intensity normalization, pixel spacing normalization and rescaling to produce the standardized small image patches.

3. The apparatus of any preceding embodiment, wherein the convolution neural network (CNN) method is pre-trained.

4. The apparatus of any preceding embodiment, wherein the pre-trained convolution neural network (CNN) method comprises OverFeat.

5. The apparatus of any preceding embodiment, wherein the second order classification comprises a Gaussian radial basis function kernel SVM classification of combined first order classification data and one or more standard imaging features selected from the group of features consisting of: skewness of intensity histograms in T2w images; an average ADC value; lowest $10^{th}$ percentile; an average $K^{trans}$; highest $10^{th}$ percentile $K^{trans}$ value; and region of interest size in T2w images.

6. A computer implemented method for detecting and grading carcinoma, the method comprising: (a) acquiring a plurality of magnetic resonance images of a subject; (b) pre-processing the acquired images; (c) applying a convolution neural network (CNN) method to extract deep learning features from the pre-processed images; (d) applying support vector machine (SVM) classifiers to the extracted deep learning features to produce SVM decision values; and (e) obtaining a Gaussian radial basis function (RBF) kernel SVM classification of combined support vector machine (SVM) decision values and statistical features to produce a final decision; and (f) wherein the method is performed by a computer processor executing instructions stored on a non-transitory computer-readable medium.

7. The method of any preceding embodiment, wherein the magnetic resonance images comprise multi-parametric MRI (mp-MRI) images.

8. The method of any preceding embodiment, wherein the pre-processing comprises: (a) pixel intensity normalization; (b) pixel spacing normalization; and (c) rescaling.

9. The method of any preceding embodiment, wherein the convolution neural network (CNN) method is pre-trained.

10. The method of any preceding embodiment, wherein the pre-trained convolution neural network (CNN) method comprises OverFeat.

11. The method of any preceding embodiment, wherein the applying a convolution neural network (CNN) method to extract deep learning features from the pre-processed images comprises extracting deep learning features from T2-weighted (T2w), apparent diffusion coefficient (ADC) and $K^{trans}$ data of standardized small image patches.

12. The method of any preceding embodiment, wherein the applying support vector machine (SVM) classifiers to the extracted deep learning features to produce SVM decision values comprises obtaining a prediction score for each set of deep learning features by applying a first order classification of support vector machine (SVM) classifiers.

13. The method of any preceding embodiment, wherein the support vector machine (SVM) decision values are combined with one or more statistical features (fs) from the group of statistical features consisting of: (a) skewness of intensity histograms in T2w images; (b) average ADC value; (c) lowest $10^{th}$ percentile; (d) ADC value; (e) average $K^{trans}$; (f) highest $10^{th}$ percentile $K^{trans}$ value; and (g) ROI size in T2w images.

14. A computer readable non-transitory medium storing instructions executable by a computer processor, the instructions when executed by the computer processor performing steps comprising: (a) acquiring a plurality of multi-parametric MRI (mp-MRI) images of a subject; (b) preprocessing the images to produce standardized small image patches; (c) extracting deep learning features from T2-weighted (T2w), apparent diffusion coefficient (ADC) and $K^{trans}$ data of the standardized small image patches with a convolution neural network (CNN); (d) obtaining a prediction score for each set of deep learning features by applying a first order classification of support vector machine (SVM) classifiers; and (e) applying as second order classification of a Gaussian radial basis function kernel SVM classification of combined first order classification data to produce a final classification.

15. The medium of any preceding embodiment, wherein the pre-processing of mp-MRI images instructions further comprise pre-processing the mp-MRI images with pixel intensity normalization, pixel spacing normalization and rescaling to produce the standardized small image patches.

16. The medium of any preceding embodiment, wherein the convolution neural network (CNN) method is pre-trained.

17. The medium of any preceding embodiment, wherein the pre-trained convolution neural network (CNN) method comprises OverFeat.

18. The medium of any preceding embodiment, wherein the second order classification comprises a Gaussian radial basis function kernel SVM classification of combined first order classification data and one or more standard imaging features selected from the group of features consisting of: skewness of intensity histograms in T2w images; an average ADC value; lowest $10^{th}$ percentile; an average $K^{trans}$; highest $10^{th}$ percentile $K^{trans}$ value; and region of interest size in T2w images.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server or all or a portion of the instructions can be stored locally and remotely. Instructions stored remotely can be downloaded (pushed) to the device by user initiation, or automatically based on one or more factors.

It will further be appreciated that as used herein, that the terms processor, computer processor, central processing unit (CPU), and computer are used synonymously to denote a device capable of executing the instructions and communicating with input/output interfaces and/or peripheral devices, and that the terms processor, computer processor, CPU, and computer are intended to encompass single or multiple devices, single core and multicore devices, and variations thereof.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

Summary of Mean Classification Performance

| Mean Performance | Disclosed Method | $f_{T2}$ | $f_{ADC}$ | $f_K$ | $f_s$ |
|---|---|---|---|---|---|
| AUC | 0.922 | 0.926 | 0.890 | 0.899 | 0.660 |
| Accuracy | 0.904 | 0.827 | 0.821 | 0.830 | 0.617 |
| Sensitivity | 0.876 | 0.837 | 0.757 | 0.808 | 0.600 |
| Specificity | 0.955 | 0.833 | 0.923 | 0.875 | 0.665 |

TABLE 2

Matlab Code

```
%%%%%%%%%%%%%%%%%%%%%%%%%%%%%%%%%%%%%%%%%%%
%%%%%%%%%%%%%%%%%%%%%%%%%%%%%%%%
%    This code requires Matlab and depends on two external libraries:
%         1) OverFeat      cilvr.nyu.edu/doku.php?id=code:start
%         2) LibSVM        www.csie.ntu.edu.tw/~cjlin/libsvm/
%
%                Authors: Xinran Zhong, Shiwen Shen, William Hsu, Kyung Sung
%                Radiological Sciences, UCLA
%
%
%    The overall script runs as follows for each case:
%              FeatureToAdd = TakeFeature(T2,ADC,Ktrans);
%              for each modality
%                       JPG = Prepro(DICOM)
%                       Get deep feature from command = BashFileOverfeat(ImageName)
%              end
%
%    (label: m*1 vector with m number of cases)
%    (feature: m*n matrix with m number of cases and n number of features for each case)
%
%%%%%%%%%%%%%%%%%%%%%%%%%%%%%%%%%%%%%%%%%%%
%%%%%%%%%%%%%%%%%%%%%%%%%%%%%%%%
%% Step 1: Generate the region of interest (square)
%
%    For each lesion, the input is a bounding box, which contains
%    the lesion across each imaging (ADC, Ktrans, T2).
%    All pixel values outside of the bounding box are set to zero.
%
%         NOTE: Our method can be generaliazable to include any other imaging
%         components in multi-parametric MRI (mp-MRI).
%
%    Input:   ADC, Ktrans, T2 images
%    Output:  Region of interest masked images (0 value for background)
%%%%%%%%%%%%%%%%%%%%%%%%%%%%%%%%%%%%%%%%%%%
%%%%%%%%%%%%%%%%%%%%%%%%%%%%%%%
%    Step 2: Extract statistical features from each ROI
%
%    For each of lesion, generate statistical features:
%                 skewness-of-intensity histogram in T2w images,
%                 average ADC value,
%                 lowest 10th percentile ADC value,
%                 average Ktrans,
%                 highest 10th percentile Ktrans value,
%                 ROI size in T2w images.
%
%         NOTE: We illustrate and demonstrate our approach using the above
%         statistical features, but our method can be generalizable to
%         other standard imaging features.
%
%    Input:   Pixel values within the ROW defined in Step 1
%    Output:  Statistical features calculated from each ROI
function FeatureToAdd = TakeFeature(T2,ADC,Ktrans)
```

TABLE 2-continued

Matlab Code

```
    T2_ROI = find_ROI(T2); % find_ROI is a function that identifies the non-zero
regions in the image
    [x_T2, y_T2] = size(T2_ROI);
    size_T2 = x_T2*y_T2;
    % Skewness of T2
    T2_ROI = reshape(T2_ROI,x_T2*y_T2,1);
    T2_skewness = skewness(T2_ROI);
    % Average ADC value
    ADC_ROI = find ROI(ADC);
    [x_ADC, y_ADC] = size(ADC_ROI);
    ADC_ROI = reshape(ADC_ROI,x_ADC*y_ADC,1);
    ADC_average = mean(ADC_ROI);
    % 10th percentile of the lowest ADC value
    ADC_ROI = sort(ADC_ROI);
    n = round(x_ADC*y_ADC/10);
    ADC_10 = ADC_ROI(n);
    % Average ADC value
    Ktrans_ROI = find_ROI(Ktrans);
    [x_Ktrans, y_Ktrans] = size(Ktrans_ROI);
    Ktrans_ROI = reshape(Ktrans_ROI,x_Ktrans*y_Ktrans,1);
    Ktrans_average = mean(Ktrans_ROI);
    % 10th percentile of the highest Ktrans Value
    Ktrans_ROI = sort(Ktrans_ROI,'descend');
    n = round(x_Ktrans*y_Ktrans/10);
    Ktrans_10 = Ktrans_ROI(n);
    FeatureToAdd = [size_T2, T2_skewness, ADC_average, ADC_10,
Ktrans_average, Ktrans_10]';
end
%%%%%%%%%%%%%%%%%%%%%%%%%%%%%%%%%%%%%%%%%%%%%
%%%%%%%%%%%%%%%%%%%%%%%%%%%%%%%%
%   Step 3: Save each DICOM to png and pre-process them
%
%   Preprocess each image into format that is capable of being processed
%   using Overfeat (e.g., Size 231*231, RBG channel and intensity range [0 255])
%
%
%   Input:   Images of each ROI
%   Output:  Image in .png format
function X = Prepro(A)
    % resize
    A = imresize(A,[231,231]);
    A = im2double(A);
    A(find(A<0)) = 0;
    % rescale
    A = round((A − min(A(:)))/(max(A(:))−min(A(:))) *255);
    X = A;
    X(:,:,2) = X;
    X(:,:,3) = X(:,:,1);
    X = uint8(X);
end
%%%%%%%%%%%%%%%%%%%%%%%%%%%%%%%%%%%%%%%%%%%%%
%%%%%%%%%%%%%%%%%%%%%%%%%%%%%%%%
%   Step 4: Use OverFeat to extract deep features for each image
%
%   For each png image, run OverFeat commands
%
%       NOTE: OverFeat is used in this implementation as an example.
%       Our method can be generalizable to both any "pre-trained"
%       and "non-pre-trained" convolutional neural networks (CNN) methods
%       (or classifiers, more broadly), depending on availabilities of
%       labeled training data that can attain sufficient feature learning.
%
%
%   Input:   File path of exported PNG images
%   Output:  Command line statements to execute OverFeat
function BashFileOverfeat(ImageName)
DirectPath = 'cd /Users/xinranzhong/Documents/phd/tools/Overfeat/overfeat/src/';
fprintf(fid,'%s\n', DirectPath);
OutputName = strcat(ImageName,\u2019.txt');
fprintf(fid, './overfeat −f %s −L 20 > %s;\n',ImageName, OutputName);
%%%%%%%%%%%%%%%%%%%%%%%%%%%%%%%%%%%%%%%%%%%%%
%%%%%%%%%%%%%%%%%%%%%%%%%%%%%
%   Step 5: Use LibSVM to train the model
%
%   Use the feature generated using the deep classifier (i.e., OverFeat) to train the
two layer SVM classier
%   and evaluate using five-fold cross validation.
```

TABLE 2-continued

Matlab Code

```
%           1) Generate 'train1' for linear SVM training, 'train2' for RBF SVM training
and 'test' for testing
%           2) Train three linear SVMs with leave-one-out cross validation using 'train1'
and find the best C for all three classifiers.
%           3) Generate Probability Feature from three linear SVMs as new features for
'train2' and 'test'
%           4) Cross validate RBF SVM
%
%   Input:  Label vector for each case
%   Output: Accuracy and area under curve
%%% 1) Randomly split data into five folds:
%           "train1" for linear SVM training
%           "train2" for RBF SVM training
%           "test" for testing
for i = 1: 5
    train_ind = randperm(length(LabelT2));
    %%% Five-fold cross validation
    partition = length(train_ind)/5;
    for i = 1: 5
        % split into different data sets
        ind(i).test = train_ind(((i−1 )*partition + 1 : i*partition));
        ind(i).train = setdiff(train_ind,ind(i).test);
        ind(i).train =ind(i).train(randperm(size(ind(i).train,1)),:);
        ind(i).train1 = ind(i).train(1: 2*partition);
        ind(i).train2 = ind(i).train(2*partition :end);
    end
    %%% 2) Train three linear SVM with leave-one-out cross validation
    %   and find the best C for all of the three classifier.
    % Train each linear SVM
    for i = 1:5
        v = 10;
        t = 0;
        % "myCV_SVM" is a function for cross-validation;
        [bestcv_T2(i), cmd1] = myCV_SVM(LabelT2(ind(i).train1,1),
FeatureT2(ind(i).train1,:), v, t);
        [bestcv_ADC(i), cmd2] = myCV_SVM(LabelADC(ind(i).train1,1),
FeatureADC(ind(i).train1,:), v, t);
        [bestcv_Ktrans(i),cmd3] = myCV_SVM(LabelKtrans(ind(i).train1,1),
FeatureKtrans(ind(i).train1,:), v, t);
        cmd_first(i).cmd1 = cmd1;
        cmd_first(i).cmd2 = cmd2;
        cmd_first(i).cmd3 = cmd3;
    end
    % Find optimal parameters
    [X, T2_index] = max(bestcv_T2);
    cmd_T2 = [cmd_first(T2_index).cmd1, ' −b 1'];      % Classifier 1
    [X, ADC_index] = max(bestcv_ADC);
    cmd_ADC = [cmd_first(ADC_index).cmd2, ' −b 1'];    % Classifier 2
    [X, Ktrans_index] = max(bestcv_Ktrans);
    cmd_Ktrans = [cmd_first(Ktrans_index).cmd3, ' −b 1'];  % Classifier 3
    %%% 3) Generate Probability Feature from three linear SVMs as new features
    for i = 1:5
        model(i).T2 = svmtrain(LabelT2(ind(i).train1,1), FeatureT2(ind(i).train1,:),
cmd_T2);
        [predicted_label, accuracy, prob_T2] = svmpredict(LabelT2(ind(i).train2,1),
FeatureT2(ind(i).train2,:), model(i).T2,' −b 1');
        [predicted_label, accuracy, prob_T2_t] = svmpredict(LabelT2(ind(i).test,1),
FeatureT2(ind(i).test,:), model(i).T2,' −b 1');
        model(i).ADC = svmtrain(LabelADC(ind(i).train1,1),
FeatureADC(ind(i).train1,:), cmd_ADC);
        [predicted_label, accuracy, prob_ADC] =
svmpredict(LabelADC(ind(i).train2,1), FeatureADC(ind(i).train2,:), model(i).ADC,' −
b 1');
        [predicted_label, accuracy, prob_ADC_t] =
svmpredict(LabelADC(ind(i).test,1), FeatureADC(ind(i).test,:), model(i).ADC,' −b
1');
        model(i).Ktrans = svmtrain(LabelKtrans(ind(i).train1,1),
FeatureKtrans(ind(i).train1,:), cmd_Ktrans);
        [predicted_label, accuracy, prob_Ktrans] =
svmpredict(LabelKtrans(ind(i).train2,1), FeatureKtrans(ind(i).train2,:),
model(i).Ktrans,' −b 1');
        [predicted_label, accuracy, prob_Ktrans_t] =
svmpredict(LabelKtrans(ind(i).test,1), FeatureKtrans(ind(i).test,:), model(i).Ktrans,'
−b 1');
        ProbT2(:,i) = prob_T2(:,1);
        ProbADC(:,i) = prob_ADC(:,1);
        ProbKtrans(:,i) = prob_Ktrans(:,1);
        ProbT2Test(:,i) = prob_T2_t(:,1);
```

TABLE 2-continued

Matlab Code

```
            ProbADCTest(:,i) = prob_ADC_t(:,1);
            ProbKtransTest(:,i) = prob_Ktrans_t(:,1);
        end
%%% 4) Five-fold cross validation for RBF SVM
bestcv = 0;
for log2c = −5:15, % Parameter searching range from LibSVM
        for log2g = 3:−1:−15, % Parameter searching range from LibSVM
                cmd = [' −c', num2str(2^log2c), ' −g ', num2str(2^log2g),' −t 2'];
                cv = 0;
                for i = 1: 5
                        instance_two_train = [ProbT2(:,i), ProbADC(:,i), ProbKtrans(:,i)];
                        instance_two_test = [ProbT2Test(:,i), ProbADCTest(:,i),
ProbKtransTest(:,i)];
                        model = svmtrain(LabelT2(ind(i).train2,1), instance_two_train, cmd);
                        [predicted_label, cvOne, prob_estimates] =
svmpredict(LabelT2(ind(i).test,1), instance_two_test, model);
                        cv = cv + cvOne(1);
                end
                cv = cv / 5;
                if (cv >= bestcv),
                        bestcv = cv; bestc = 2^log2c; bestg = 2^log2g;
                        cmdout = [' −c', num2str(bestc), ' −g ', num2str(bestg),' −t ',num2str(t)];
                end
        end
    end
end
```

What is claimed is:

1. An apparatus for detecting and grading carcinoma, comprising:
   (a) a computer processor; and
   (b) a non-transitory computer-readable memory storing instructions executable by the computer processor;
   (c) wherein said instructions, when executed by the computer processor, perform steps comprising:
      (i) acquiring a plurality of multi-parametric MRI (mp-MRI) images of a subject with an mp-MRI imager;
      (ii) pre-processing the acquired mp-MRI images to produce standardized small image patches;
      (iii) extracting deep learning features from T2-weighted (T2w), apparent diffusion coefficient (ADC) and $K^{trans}$ data of the standardized small image patches with a convolution neural network (CNN) method;
      (iv) obtaining a prediction score for each set of deep learning features by applying a first order classification of support vector machine (SVM) classifiers; and
      (v) applying as second order classification of a Gaussian radial basis function kernel SVM classification of combined first order classification data to produce a final classification.

2. The apparatus of claim 1, wherein said pre-processing of mp-MRI images instructions further comprise pre-processing the mp-MRI images with pixel intensity normalization, pixel spacing normalization and rescaling to produce said standardized small image patches.

3. The apparatus of claim 1, wherein said convolution neural network (CNN) method is pre-trained.

4. The apparatus of claim 3, wherein said pre-trained convolution neural network (CNN) method comprises OverFeat.

5. The apparatus of claim 1, wherein said second order classification comprises a Gaussian radial basis function kernel SVM classification of combined first order classification data and one or more standard imaging features selected from the group of features consisting of: skewness of intensity histograms in T2w images; an average ADC value; lowest $10^{th}$ percentile; an average $K^{trans}$, highest $10^{th}$ percentile $K^{trans}$ value; and region of interest size in T2w images.

6. A computer implemented method for detecting and grading carcinoma, the method comprising:
   (a) acquiring a plurality of magnetic resonance images of a subject;
   (b) pre-processing the acquired images;
   (c) applying a convolution neural network (CNN) method to extract deep learning features from said pre-processed images;
   (d) applying support vector machine (SVM) classifiers to the extracted deep learning features to produce SVM decision values; and
   (e) obtaining a Gaussian radial basis function (RBF) kernel SVM classification of combined support vector machine (SVM) decision values and statistical features to produce a final decision; and
   (f) wherein said method is performed by a computer processor executing instructions stored on a non-transitory computer-readable medium.

7. The method of claim 6, wherein said magnetic resonance images comprise multi-parametric MRI (mp-MRI) images.

8. The method of claim 6, wherein said pre-processing comprises:
   (a) pixel intensity normalization;
   (b) pixel spacing normalization; and
   (c) rescaling.

9. The method of claim 6, wherein said convolution neural network (CNN) method is pre-trained.

10. The method of claim 9, wherein said pre-trained convolution neural network (CNN) method comprises OverFeat.

11. The method of claim 7, wherein said applying a convolution neural network (CNN) method to extract deep learning features from said pre-processed images comprises extracting deep learning features from T2-weighted (T2w), apparent diffusion coefficient (ADC) and $K^{trans}$ data of standardized small image patches.

12. The method of claim 7, wherein said applying support vector machine (SVM) classifiers to the extracted deep learning features to produce SVM decision values comprises obtaining a prediction score for each set of deep learning features by applying a first order classification of support vector machine (SVM) classifiers.

13. The method of claim 11, wherein said support vector machine (SVM) decision values are combined with one or more statistical features (fs) from the group of statistical features consisting of:
    (a) skewness of intensity histograms in T2w images;
    (b) average ADC value;
    (c) lowest $10^{th}$ percentile;
    (d) ADC value;
    (e) average $K^{trans}$;
    (f) highest $10^{th}$ percentile $K^{trans}$ value; and
    (g) ROI size in T2w images.

14. A non-transitory computer readable medium storing instructions executable by a computer processor, said instructions when executed by the computer processor performing steps comprising:
    (a) acquiring a plurality of multi-parametric MRI (mp-MRI) images of a subject;
    (b) preprocessing the images to produce standardized small image patches;
    (c) extracting deep learning features from T2-weighted (T2w), apparent diffusion coefficient (ADC) and $K^{trans}$ data of the standardized small image patches with a convolution neural network (CNN);
    (d) obtaining a prediction score for each set of deep learning features by applying a first order classification of support vector machine (SVM) classifiers; and
    (e) applying as second order classification of a Gaussian radial basis function kernel SVM classification of combined first order classification data to produce a final classification.

15. The medium of claim 14, wherein said pre-processing of mp-MRI images instructions further comprise pre-processing the mp-MRI images with pixel intensity normalization, pixel spacing normalization and rescaling to produce said standardized small image patches.

16. The medium of claim 14, wherein said convolution neural network (CNN) method is pre-trained.

17. The medium of claim 16, wherein said pre-trained convolution neural network (CNN) method comprises OverFeat.

18. The medium of claim 14, wherein said second order classification comprises a Gaussian radial basis function kernel SVM classification of combined first order classification data and one or more standard imaging features selected from the group of features consisting of: skewness of intensity histograms in T2w images; an average ADC value; lowest $10^{th}$ percentile; an average $K^{trans}$, highest $10^{th}$ percentile $K^{trans}$ value; and region of interest size in T2w images.

19. The method of claim 7, wherein said pre-processing comprises:
    (a) pixel intensity normalization;
    (b) pixel spacing normalization; and
    (c) rescaling.

20. The method of claim 7, wherein said convolution neural network (CNN) method is pre-trained.

21. The method of claim 20, wherein said pre-trained convolution neural network (CNN) method comprises OverFeat.

* * * * *